United States Patent [19]
Nelson

[11] Patent Number: 4,663,486
[45] Date of Patent: May 5, 1987

[54] CONVERSION OF PROSTAGLANDIN ANALOGS INTO A BICARBONATE INSOLUBLE OLIGOMERIC MIXTURE

[75] Inventor: George L. Nelson, Narberth, Pa.

[73] Assignee: The United States of America as represented by the Secretary of the Navy, Washington, D.C.

[21] Appl. No.: 492,088

[22] Filed: May 6, 1983

[51] Int. Cl.$^4$ ............................................. C07C 45/70
[52] U.S. Cl. .................................... 568/353; 568/379
[58] Field of Search .............................. 568/353, 379

[56] References Cited

U.S. PATENT DOCUMENTS 4,245,111 1/1981 Polis et al. ........................ 560/121
4,338,466 7/1982 Nelson ............................... 568/379

Primary Examiner—James H. Reamer
Attorney, Agent, or Firm—Prithvi C. Lall; Arthur A. McGill; Michael J. McGowan

[57] ABSTRACT

A method for oligomerization of a group of prostaglandin analogs such as the Ethyl Analog 3-(trans-3-keto-1-pentenyl)-2-ethyl-2-cyclopentenone into a biologically active exhibiting protection of oxidative phosphorylation of degenerated mitochondria and sodium bicarbonate insoluble oligomeric mixtures is described. The Ethyl Analog is treated with ethanolic potassium hydroxide solution in an oxygen-free atomsphere at moderate conditions of temperature, time and concentration.

6 Claims, No Drawings

CONVERSION OF PROSTAGLANDIN ANALOGS INTO A BICARBONATE INSOLUBLE OLIGOMERIC MIXTURE

STATEMENT OF GOVERNMENT INTEREST

The invention described herein may be manufactured and used by or for the Government of the United States of America for governmental purposes without the payment of royalties thereon or therefor.

Subject patent application is related by my co-pending application Ser. No. 492,087, filed May 6, 1983 and entitled CONVERSION OF PROSTAGLANDIN ANALOGS INTO A BICARBONATE SOLUBLE OLIGOMERIC MIXTURE.

BACKGROUND OF THE INVENTION (1) Field of the Invention

This invention is related to prostaglandin analogs and method of preparation thereof, as precursors for the synthesis of oligomeric mixtures showing biological activity with regard to restoration of oxidative phosphorylation in the degenerated mitochondria and more particularly to oligomerization of the Ethyl Analog having low molecular weights which give rise to oligomeric mixture having various components thereof biologically active in vitro.

(2) Description of the Prior Art

A new class of polymeric derivatives designated $PGB_x$ and the syntheses thereof are disclosed in U.S. Pat. No. 4,153,802 issued May 8, 1979 to David Polis et al, which have the unique property of restoring the in vitro oxidative phosphorylation ability of isolated degraded mitochondria. Furthermore, synthesis of prostaglandin analogs including the Ethyl Analog as defined below and related compounds is disclosed in U.S. Pat. No. 4,338,466 issued July 6, 1982 to George L. Nelson. All the above-identified patents are incorporated herein by reference. The analogs used in the syntheses are prostaglandins such as $PGB_1$, 13-14-dehydro-$PGB_1$ and 15-keto-$PGB_1$ methyl ester, each having a relatively complex molecular structure resulting in oligomeric derivatives which are not amenable to structural elucidation by conventional spectroscopic techniques necessary for defining the structure-activity relationships. Attempts by a number of research groups to resolve this complex mixture of oligomeric derivatives into individual components retaining biological activity have been unsuccessful.

Conversion of prostaglandin analogs such as 3-(trans-3-keto-1-pentenyl)-2-ethyl-2-cyclopentenone; hereinafter referred to as Ethyl Analog or E.A. into a higher molecular weight distribution bicarbonate soluble oligomeric mixture by treatment with ethanolic potassium hydroxide (KOH solution diluted with ethanol) with exposure to atmospheric oxygen has been tried by our group. These prostaglandin analogs are represented by:

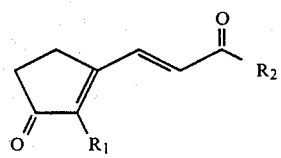

where $R_1$, and $R_2$ are members of the alkyl group. When $R_1$ and $R_2$ are $CH_2.CH_3$ each, the analog is called the Ethyl Analog (E.A.). However, the Ethyl Analog was oligomerized by treatment with ethanolic potassium hydroxide over a seven day period to give complex crude oligomeric mixture that was ca. 60 percent soluble. Both the bicarbonate soluble and insoluble fractions obtained from the crude oligomeric mixture were fractionated on Sephadex LH-20, a substrate for size exclusion chromatography. Mitochondrial activity in the protection of oxidative phosphorylation was observed for both the bicarbonate soluble and insoluble fractions with generally higher activity being observed in the bicarbonate soluble fractions. Most notably, inhibition of mitochondrial activity at higher concentrations, as is observed in the case of $PGB_x$ derived from 15-keto-$PGB_1$, was not observed for the oligomeric mixture derived from the Ethyl Analog. The activities observed for the oligomeric mixture derived from the E.A. were generally lower than those observed for 15-keto-$PGB_1$ derived $PGB_x$ at concentrations where $PGB_x$ exhibited maximum mitochondrial activity. However, at higher concentrations a greater protection was afforded by oligomeric fractions derived from the Ethyl Analog than that in the case of $PGB_x$. The mitochondrial activity for both the bicarbonate soluble and insoluble fractions derived from Sephadex LH-20 (substrate for size exclusion chromatography) chromatography was distributed throughout the fractions.

Although the above-indicated results held much potential, several serious problems remained in this method for conversion of the Ethyl Analog (E.A.) into a bicarbonate soluble oligomer possessing the ability to protect isolated mitochondria against the loss of oxidative phosphrylation. The problems were generally associated with the severe conditions (7-day treatment with ethanolic KOH) used for the conversion to a bicarbonate soluble oligomeric mixture that was a very complex mixture and not readily amenable to structural elucidation by spectroscopic methods. For this reason, a series of experiments needed to be carried out to find out how the bicarbonate insoluble oligomer fraction can be maximized while reducing the severity of the reaction conditions, what is the functionality which gives rise to bicarbonate solubility and what molecular changes are involved in oligomer formation. It was on the basis of this investigation that conditions for the conversion of the Ethyl Analog to a bicarbonate insoluble (neutral) oligomeric mixture, as described in subject patent application and for the formation of a bicarbonate soluble (acidic) oligomeric mixture, as described in my copending patent application, Ser. No. 492,087, filed May 6, 1984, were developed.

In summary, several aspects critical to the oligomerization of Ethyl Analog (E.A.) resulted from these investigations. It has been determined that sufficient exposure to oxygen is required for formation of the functionality responsible for bicarbonate solubility. This functionality has been identified as the carboxylic acid although the detailed mechanistic mode of formation of this acidic functional group from the neutral Ethyl Analog is not completely defined. Taking advantage of this information, the Ethyl Analog could be oligomerized to high conversions of bicarbonate soluble oligomer (greater than 80 percent) under relatively mild conditions (3–6 hours at 50° C.) if sufficient exposure to atmospheric oxygen was provided.

SUMMARY OF THE INVENTION

The method of conversion of the Ethyl Analog into a high molecular weight distribution bicarbonate soluble oligomeric mixture by treatment with ethanolic potassium hydroxide with exposure to atmospheric oxygen, according to the teachings of subject invention includes treatment of the Ethyl Analog (E.A.) with ethanolic potassium hydroxide solution under mild condition of 50° C. in a constant temperature bath in an atmosphere free of oxygen. The reaction is quenched by the addition of dilute hydrochloric acid to lower the pH of the solution mixture is extracted several times with ethyl acetate. The combined sodium bicarbonate extracts are then studied for oxidative phosphorylation of degenerated mitochondria in vitro.

An object of subject invention is to have a new technique for converting the Ethyl Analog (E.A.) into a higher molecular weight distribution sodium bicarbonate insoluble oligomeric mixture which is active in oxidative phosphorylation of degenerated mitochondria.

Another object of subject invention is to have a method for converting the Ethyl Analog (E.A.) into high molecular weight sodium bicarbonate insoluble oligomeric mixture by treatment with ethanolic potassium hydroxide with exposure to atmospheric oxygen.

Still another object of subject invention is to have a new technique for converting the Ethyl Analog in a higher molecular weight distribution which is formed under mild temperature conditions.

Still another object of subject invention is to oligomerize the Ethyl Analog (E.A.) into a biologically active oligomeric mixture where the time for the reaction to reach completion is relatively short.

Other objects, advantages and novel features of the invention will become apparent from the following detailed description of the invention.

DESCRIPTION OF A PREFERRED EMBODIMENT

A process for polymerizing the Ethyl Analog (E.A.) according to the teachings of subject invention includes treatment of the Ethyl Analog (E.A.) with an ethanolic solution of potassium hydroxide under mild conditions and for relatively short period. The reaction is then stopped by making the solution acidic, thus reducing the pH value thereof. The reaction is conducted in oxygen-free an atmosphere and is accomplished under nitrogen after effectively removing residual oxygen using the standard freeze-thaw technique. The quenched reaction mixture is diluted with water and extracted several times with ethyl acetate followed by further extraction with sodium bicarbonate solution. The combined bicarbonte extracts are further washed with water until neutral and dried. Ethyl acetate is then removed under reduced pressure to yield a crude bicarbonate insoluble, biologically active oligomeric mixture.

The new technique according to the teachings of subject invention is illustrated by the following example which should be regarded as being carried out under a representative set of conditions rather than an exclusive set of conditions that will result in the conversion of the Ethyl Analog (E.A.) into the described oligomeric mixture. It should be further understood that changes in the concentration of either the Ethyl Analog or potassium hydroxide solution as well as the reaction temperature and time are inter-dependent so that a change in one of the above variables can be compensated by a corresponding change in the other variables. However, the exclusion of oxygen during the oligomeric reaction is considered to be essential for maximum conversion to a sodium bicarbonate insoluble oligomeric mixture under the reaction conditions described below. This can be readily accomplished if the reaction is carried out in an atmosphere of nitrogen after effectively removing residual oxygen by a conventional technique such as freeze-thaw technique. The method is illustrated by the following example:

EXAMPLE

Solutions of 500 milligrams (mg) of 3-(trans-3-keto-1-pentenyl)-2-ethyl-2-cyclopentenone (the Ethyl Analog or E.A.) in 10 milliliters (1 milliliter = 1 mL = $10^3$ liter) of absolute or pure ethanol is added 10 milliliters (mL) of 2M (molar) potassium hydroxide solution which are contained in separate reaction flasks are vigorously de-oxygenated using the freeze-thaw technique under nitrogen. After warming to room temperature, the 2M potassium hydroxide solution is transferred under positive nitrogen pressure to the Ethyl Analog solution which is maintained at 50° C. in a constant temperature bath. Reaction was observed to start immediately and the process of the conversion to a bicarbonate insoluble oligomeric mixture was monitored by ultraviolet spectroscopy which is well known in the prior art and need be discussed here. When the conversion was judged to be sufficiently complete (ca. 3-6 hours), the reaction was quenched by the addition of dilute hydrochloric acid and the pH of the reaction mixture was adjusted to 3. The quenched reaction mixture was diluted with water and extracted several times with ethyl acetate. The combined ethyl acetate extracts were extracted with 0.1M (molar) sodium bicarbonate ($NaHCO_3$) solution and washed with water until neutral. After drying, the ethyl acetate was removed under reduced pressure to yield about 90-95 percent crude sodium bicarbonate insoluble and biologically active mixture.

The crude oligomeric mixture thus obtained was chromatographed on Sephadex LH-20 using methanol as the carrier solvent. Resolution of the oligomeric mixture was not observed so that five somewhat arbitrarily selected fractions were collected. Activity in the protection of oxidative phosphorylation in isolated mitochondria was observed through all five fractions with varying degree. The highest activity was obtained in two of the five arbitrarily selected fractions. No inhibition was observed at high concentration of the oligomer.

Briefly stated, conversion of the Ethyl Analog (E.A.) under mild conditions of temperature is accomplished by mixing the Ethyl Analog with ethanolic solution of sodium hydroxide. The reaction is then quenched by using hydrochloric acid. The reaction mixture is diluted with water and extracted several times with ethyl acetate which in turn was further extracted with sodium bicarbonate solution. The ethyl acetate extracts were then washed with water, dried. Ethyl acetate was removed under pressure to yield 90 to 95 percent crude sodium bicarbonate insoluble oligomeric mixture.

Many modifications and variations of the present invention are possible in light of the above teachings. As an example, the reaction can proceed under different sets of conditions involving other concentrations of either the Ethyl Analog or potassium hydroxide solution as well as the reaction temperature and time of reaction. It is thus understood that within the scope of the appended claims the invention may be practiced otherwise than as specifically described.

What is claimed is:

1. A method for synthesizing biologically active oligomeric mixture exhibiting protection of oxidative phosphorylation of degenerated mitochondria and said oligomeric mixture being sodium bicarbonate insoluble by an oligomerization reaction of prostaglandin analogs represented by the formula:

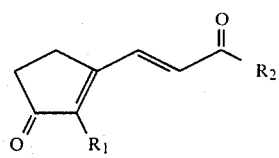

where $R_1$ and $R_2$ are members of the alkyl group;
said method includes the steps of:
treating a member of said prostaglandin analogs with ethanolic potassium hydroxide solution in oxygen-free atmosphere at 50° C. under relatively mild conditions of, time and concentration to start the oligomeric reaction;
quenching the oligomeric reaction by changing the pH of the reaction mixture by means of an acid;
extracting the reaction mixture with ethyl acetate; and
removing ethyl acetate under vacuum.

2. The method of claim 1 wherein the steps enumerated therein are applied to Ethyl Analog as one of the prostaglandin analogs represented by

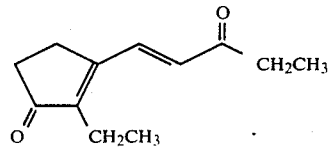

3. The method of claim 2 wherein said ethanolic potassium hydroxide solution is obtained by diluting a fixed volume of 2M potassium hydroxide solution with an equal volume of ethanol.

4. The method of claim 3 wherein the quenching of the oligomeric reaction is accomplished by treating the reaction mixture with hydrochloric acid to reduce the pH thereof to 3.

5. The method of claim 4 wherein the step of extracting with ethyl acetate further includes treating ethyl acetate extracts with 0.1M sodium bicarbonate solution.

6. The method of claim 5 wherein the step of extracting with ethyl acetate further includes treating the sodium bicarbonate extracts with water to make the oligomeric mixture neutral.

* * * * *